United States Patent
Ohira et al.

(10) Patent No.: US 6,245,959 B1
(45) Date of Patent: Jun. 12, 2001

(54) SUBSTRATE FOR ADHESIVE DRESSING, AND MEDICAL ADHESIVE DRESSING AND ADHESIVE TAPE USING THE SAME

(75) Inventors: Osamu Ohira; Takashi Kinoshita; Yasuyuki Sasaki; Takahiro Kousaka, all of Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/381,549

(22) PCT Filed: Jan. 20, 1999

(86) PCT No.: PCT/JP99/00189

§ 371 Date: Sep. 21, 1999

§ 102(e) Date: Sep. 21, 1999

(87) PCT Pub. No.: WO99/37336

PCT Pub. Date: Jul. 29, 1999

(30) Foreign Application Priority Data

Jan. 21, 1998 (JP) .................................................. 10-009605

(51) Int. Cl.⁷ ...................................................... A61F 13/00
(52) U.S. Cl. ................................. 602/41; 602/42; 602/43; 602/44; 602/45; 602/46
(58) Field of Search ........................ 602/41–47; 428/343, 428/349; 260/42.1

(56) References Cited

U.S. PATENT DOCUMENTS 4,346,700 * 8/1982 Dunshee et al. .

FOREIGN PATENT DOCUMENTS

| WO 97/42258 | * 11/1997 | (EP) . |
|---|---|---|
| 58-67776 | 4/1983 | (JP) . |
| 1-299214 | 12/1989 | (JP) . |
| 4-300822 | 10/1992 | (JP) . |
| 7-268294 | 10/1995 | (JP) . |

* cited by examiner

*Primary Examiner*—Michael A. Brown
*Assistant Examiner*—Lalita M. Hamilton
(74) *Attorney, Agent, or Firm*—Sughrue, Mion, Zinn, Macpeak & Seas, PLLC

(57) ABSTRACT

A substrate for an adhesive dressing comprising an ethylene/vinyl acetate copolymer having a weight average molecular weight of $1 \times 10^4$ to $1 \times 10^5$, a molecular weight distribution of 4.0 or less, a melt flow rate of 3.0 g/10 minutes or less, and a vinyl acetate content of 15 to 28% by weight is provided and a medical adhesive dressing can be prepared by forming a pressure-sensitive adhesive layer on one surface of the substrate. Further, an adhesive tape can be made by arranging a pad for covering and protecting a wounded portion, on a part of a surface of the pressure-sensitive adhesive layer.

11 Claims, No Drawings

SUBSTRATE FOR ADHESIVE DRESSING, AND MEDICAL ADHESIVE DRESSING AND ADHESIVE TAPE USING THE SAME

TECHNICAL FIELD

The present invention relates to a substrate for an adhesive dressing used for application to the skin in medical sanitary field or the like, a medical adhesive dressing and an adhesive tape (also termed as "adhesive plaster" or "bandage"),e.g.,a first-aid adhesive tape, using the same. More particularly, the present invention relates to a substrate for an adhesive dressing having excellent feeling and mechanical strength, which is used in an adhesive tape, a large-sized adhesive tape, a dressing material, a drape material or the like, and can be utilized in a medical adhesive dressing and an adhesive tape.

BACKGROUND ART

A medical adhesive dressing generally comprises a substrate film and a pressure-sensitive adhesive layer formed on one side of the substrate film and is adhered to a skin surface to be applied through the pressure-sensitive adhesive layer upon use.

Most substrates conventionally employed in adhesive dressings for such a medical use comprise a soft polyvinyl chloride as a main component in view of a skin follow-up property (flexibility), a stretchability, hand and drape or the like while they are adhered.

However, soft polyvinyl chlorides generally contain one or more plasticizers such as dioctyl phthalate in large amounts in order to impart flexibility to a film that is formed. Many problems have been pointed out that migration of the plasticizer(s) into a pressure-sensitive adhesive layer decreases the cohesive force of a pressure-sensitive adhesive layer, which causes a phenomenon that an adhesive remains on the skin or decreases the adhesion strength of the pressure-sensitive adhesive layer. On the other hand, in recent years, importance has been increasingly attached to environmental problems and from this standpoint, various attempts have been made in every field to use less amounts of polyvinyl chloride resins, which contain chlorine atoms, i.e., species of halogen.

Further, in the case where it is attempted to use an adhesive tape with a film substrate comprising a polyvinyl chloride resin by winding it around a site that is in a brisk motion, such as a joint portion of fingers, the adhesive tape elongates in a proper degree when it is affixed so that it can be wound around the site fittingly. However, since the adhesive tape has a low shrinkage rate and is susceptible to a stress relaxation, a gap is gradually caused between the adhered surface and the adhesive tape after the affixing. As a result, the adhesive tape may fall out from the finger or the like site, or the position of the adhesive tape may shift. Further, since the polyvinyl chloride resin has a high temperature-sensitivity, the film substrate becomes harder in the winter seasons, so that it may happen that the face of a user is injured while he or she washes his or her face.

Therefore, a substrate film for an adhesive dressing with a polyolefin-based resin as a substitute resin for polyvinyl chloride has come to be examined.

In order to obtain a flexibility equal to that of the polyvinyl chloride resin film in the substrate film comprising the above-mentioned substitute resin, various attempts have been made such as reduction in the thickness of the substrate film or mixing an elastomer component to impart stretchability. However, the resulting substrate film is insufficient in mechanical strength, and it cannot be peeled off cleanly when it is peeled after it is affixed and used. As a result, the substrate film may be torn off.

In order to improve such a poor mechanical strength, it has been attempted to provide a substrate film of multilayer structure and form a resin layer having a relatively high strength as an inner layer thereof. However, the problem may arise that the substrate film curls or the substrate film is difficult to affix since it easily curls by the stress when removing a release paper.

As a result of extensive investigations with view to solving the problem on the conventional substrate film comprising polyvinyl chloride and the problem on the substrate film comprising a polyolefin-based resin as a substitute therefor, the present inventors have found that use of an ethylene/vinyl acetate copolymer having specified properties as a film substrate can provide a medical adhesive dressing or an adhesive tape that satisfies the desired characteristics such as flexibility, stretchability, mechanical strength, curl prevention property and the like, thus having completed the present invention.

DISCLOSURE OF THE INVENTION

Accordingly, the present invention is to provide a substrate for an adhesive dressing, characterized by comprising an ethylene/vinyl acetate copolymer having a weight average molecular weight (Mw) of $1\times10^4$ to $1\times10^5$, a molecular weight distribution (Mw/Mn) of 4.0 or less, a melt flow rate (MFR) of 3.0 g/10 minutes or less, and a vinyl acetate content of 15 to 28% by weight.

Further, the present invention is to provide a medical adhesive dressing comprising the above-mentioned substrate for an adhesive dressing and a pressure-sensitive adhesive layer formed on one side of the substrate and also an adhesive tape having a pad for protecting a wounded portion arranged on a part of the surface of the pressure-sensitive adhesive layer.

BEST MODE FOR CARRYING OUT THE INVENTION

The substrate for an adhesive dressing of the present invention is obtained by molding an ethylene/vinyl acetate copolymer having a weight average molecular weight (Mw) of $1\times10^4$ to $1\times10^5$, a molecular weight distribution (Mw/Mn) of 4.0 or less, a melt flow rate (MFR) of 3.0 g/10 minutes or less, and a vinyl acetate content of 15 to 28% by weight into a sheet form by a calendering method, an inflation method, an extrusion method or the like. As the sheet formation method, it is preferable to use a calendering method from the viewpoints of ease of molding a resin having a poor flowability (MFR$\leq$3.0 g/10 minutes) as in the present invention into a sheet form and of ease of processing when subjecting the molded sheet to embossing finish.

In the present invention, adjustment of vinyl acetate content in the ethylene/vinyl acetate copolymer to 15 to 28% by weight, preferably 20 to 25% by weight, can inhibit crystallization of the copolymer resin, so that a substrate having moderate elasticity and flexibility imparted thereto can be obtained. If the vinyl acetate content is less than 15% by weight, the copolymer has properties like those of a soft polyethylene, and thus has poor flexibility. On the other hand, if the vinyl acetate content exceeds 28% by weight, flexibility is improved, but the substrate obtained tends to exhibit pressure-sensitive properties. As a result, the phenomenon of blocking among substrates occurs during the production process or use feeling becomes poor, which is unpreferable. Further, the mechanical strength is gradually decreased, and this is also unpreferable.

Further, the ethylene/vinyl acetate copolymer used in the present invention has the greatest characteristics that the weight average molecular weight (Mw) is $1 \times 10^4$ to $1 \times 10^5$, preferably $4.5 \times 10^4$ to $9.5 \times 10^4$, and the molecular weight distribution (Mw/Mn) is a relatively narrow molecular weight distribution of 4.0 or less, preferably 3.5 or less. In the present invention, the tendency is observed that if Mw exceeds the above upper limit, the flexibility decreases, and if Mw is below the lower limit, the mechanical strength becomes insufficient, which are unpreferable. Further, if Mw/Mn exceeds 4.0, it is insufficient in mechanical strength. In many cases, the ethylene/vinyl acetate copolymers generally used have a molecular weight distribution exceeding 4.3.

The ethylene/vinyl acetate copolymer used in the present invention is characterized by not only satisfying the above-mentioned characteristics, but also having a poor flowability of 3.0 g/10 minutes or less in melt flow rate (MFR). MFR has a relatively high correlation with the tensile strength of a resultant film and also with the above-mentioned Mw. Generally, if MFR is 3.0 g/10 minutes or less, the substrate comprising the ethylene/vinyl acetate copolymer having Mw in the range of $1 \times 10^4$ to $1 \times 10^5$ has a pull strength of 130 kgf/cm$^2$ or more, but the pull strength does not yet reach the practically required value of 200 kgf/cm$^2$ or more. In addition, only a substrate having a thickness within a specified range can provide the above-mentioned pull strength. In the present invention, a substrate sheet having balanced flexibility, stretchability, mechanical strength and the like can be obtained if the copolymer has a relatively narrow molecular weight distribution such that the Mw/Mn is 4.0 or less, even when it is molded into a sheet form with a desired thickness.

Ethylene/vinyl acetate copolymers having a relatively broad molecular weight distribution as generally used, for example, a copolymer having an Mw/Mn of 4.4, have an MFR of 1.5 g/10 minutes, and even if Mw is $9.4 \times 10^4$, which is within the numerical range of the present invention, only a substrate sheet having a pull strength of about 180 kgf/cm$^2$ is obtained. Thus, the practically required value of 200 kgf/cm$^2$ is not obtained.

Therefore, it is important for the ethylene/vinyl acetate copolymer used in the present invention to have the physical values of the numerical range as specified in the claims (Mw is $1 \times 10^4$ to $1 \times 10^5$, Mw/Mn is 4.0 or less, and MRF is 3.0 g/10 minutes or less).

The substrate for an adhesive dressing in the present invention is one obtained by molding into a sheet form as mentioned above, and it is desirable that its thickness is 15 to 150 μm, or 50 to 150 μm, preferably 80 to 120 μm, from the viewpoints of giving less uncomfortable feeling when affixing it to a skin surface and of giving sufficient mechanical strength such as tensile strength and the like.

Further, it is preferable for the substrate for an adhesive dressing of the present invention to have a 50% modulus of 0.4 to 1.5 kgf/19 mm width and a tensile strength of 1.3 kg/19 mm width or more from the viewpoint of flexibility or follow-up property to the movement of an adhered skin surface. Also, the substrate preferably has a stress relaxing property measured under the same conditions as in the above-mentioned modulus (i.e., a ratio of the stress at 5 seconds after allowing the substrate that has been stretched 50% at 23° C. to stand to the stress at 0 second thereafter) of 60 to 95% from the point of giving an appropriate fit feeling (feeling of close adhesion with neither tight winding nor loosening) when wound around a finger as an adhesive tape, e.g., a first-aid adhesive tape or a rolled adhesive tape.

The substrate for an adhesive dressing of the present invention, which comprises the ethylene/vinyl acetate copolymer having the specified physical values as mentioned above, can be used for preparing a medical adhesive dressing by forming a pressure-sensitive adhesive layer on one side of the substrate molded into a sheet form. The pressure-sensitive adhesive layer is formed in a thickness of 20 to 80 μm, and preferably 30 to 60 μM, from the viewpoint of having adhesiveness to a skin. The pressure-sensitive adhesive to be used includes an acrylic pressure-sensitive adhesive, a natural rubber-based pressure-sensitive adhesive, a synthetic rubber-based pressure-sensitive adhesive, a silicone-based pressure-sensitive adhesive, a vinyl ether-based pressure-sensitive adhesive or the like, and is not particularly limited so long as it can be used as a medical pressure-sensitive adhesive having less skin irritation. They can be used in the form of an organic solvent type, emulsion type, hot melt type or the like. Further, these pressure-sensitive adhesives may be used alone, or a mixture of a plurality of pressure-sensitive adhesives may be used.

In preparing the above-mentioned medical adhesive dressing, one side of the substrate for an adhesive dressing of the present invention preferably is subjected to corona discharge treatment or coated with a conventional primer since this increases the wettability of the substrate to the pressure-sensitive adhesive layer to thereby improve its anchoring property. The method for forming the pressure-sensitive adhesive layer on one side of the substrate for an adhesive dressing includes a method in which a solution of the pressure-sensitive adhesive is directly coated on one side of the substrate and dried or a method in which the pressure-sensitive adhesive layer is directly formed by hot melt extrusion onto the substrate. However, in order to prevent unnecessary elongation or curl of the substrate, it is preferable to use a so-called transfer method, i.e., a method of previously forming the pressure-sensitive adhesive layer on one side of a release paper for covering and protecting the pressure-sensitive layer surface of the medical adhesive dressing obtained, by coating or extrusion, and bonding the substrate for an adhesive dressing to the surface of the pressure-sensitive adhesive layer formed.

The medical adhesive dressing of the present invention can be utilized as a dressing or a rolled adhesive tape, and also can be made an adhesive tape, e.g., a first-aid adhesive tape, by arranging a pad for protecting a wounded portion, such as a cloth (e.g., qauze) or a sponge pad, on a part of the surface of the pressure-sensitive adhesive layer.

EXAMPLES

The present invention will be explained in more detail by referring to the following Examples, but the present invention is not limited to those, and various applications can be made within the scope without departing from the technical concept of the present invention.

Examples 1–4

An ethylene/vinyl acetate copolymer having a vinyl acetate content, MFR, Mw and Mw/Mn as shown in Table 1 was used as a polymer material. A fatty ester type lubricant was blended with this material such that the amount of the lubricant was 1% by weight. The blend was melt kneaded at 130 to 150° C. and molded into a sheet form at a temperature of 120 to 140° C. by a calendering method to prepare a substrate for an adhesive dressing of the present invention.

On the other hand, an acrylic pressure-sensitive adhesive solution (solvent: ethyl acetate) having a solids content of 30% by weight was coated on a surface of a release paper which surface had been subjected to a release treatment to a dry thickness of 40 $\mu$m and dried to form a pressure-sensitive adhesive layer.

The pressure-sensitive adhesive layer formed on the release paper was transfer-laminated on one side of the substrate for an adhesive dressing obtained above to prepare a medical adhesive dressing of the present invention.

Comparative Example 1

Similarly to the above examples, a substrate for an adhesive dressing of the present invention was prepared in the same manner as in Example 2 except that an ethylene/vinyl acetate copolymer as shown in Table 1 was used and a medical adhesive dressing of the present invention was also prepared by further forming a pressure sensitive adhesive layer in the same manner as in Example 2.

Comparative Example 2

A medical adhesive dressing of the present invention was prepared in the same manner as in Example 1 except that a 80 $\mu$m-thick sheet comprising a soft vinyl chloride resin was used as a substrate for an adhesive dressing.

Comparative Example 3

A 80 $\mu$m thick sheet comprising an ethylene-methyl methacrylate copolymer resin (trade name: ACRYFT WD, a product of Sumitomo Chemical Co., Ltd.) was laminated on front and back surfaces of a 20 $\mu$m-thick sheet comprising a straight-chain, low-density polyethylene (trade name: NIPOLON LF-20, a product of Tosoh Corporation) by an inflation molding method to prepare a substrate for an adhesive dressing of a three-layer structure.

A medical adhesive dressing of the present invention was prepared as in the Example 1, except that this three-layer laminated sheet was used.

The substrates for an adhesive dressing and medical adhesive dressings obtained in the above Examples and Comparative Examples were evaluated for the following characteristics. The results are shown in Table 2.

<Stress Relaxation Property>

Each medical adhesive dressing was cut into pieces of a width of 19 mm and length of 100 mm. The cut test piece was drawn in a lengthwise direction under the condition of a drawing rate of 300 mm/minute using Tensilon tensile tester under an atmosphere of 23° C. When the test piece was elongated 50%, the test piece was allowed to stand, and a stresses at 0 second and after 5 seconds were measured. The stress after 5 seconds when the stress at 0 second was represented by 100 was shown as % value.

<50% Modulus and Tensile Strength>

Each medical adhesive dressing was cut into pieces of a width of 19 mm and a length of 100 mm. The cut test piece was drawn in a lengthwise direction under the condition of a drawing rate of 300 mm/minutes using Tensilon tensile tester under an atmosphere of 23° C. and measurement was made for 50% modulus and tensile strength (strength at break).

<Temperature-sensitivity>

Each medical adhesive dressing was cut into a test piece of a width of 19 mm and a length of 72 mm. The cut test piece was wound around the second joint of the second finger of a hand of a volunteer so as to overlap (wrapping), and an organoleptic examination was conducted at 0° C. and 23° C. The evaluation criteria are as follows.

⊚: Very soft, high fit feeling, and no uncomfortable feeling

○: Fit feeling

Δ: Slight rigid feeling

×: Very hard, and stiff uncomfortable feeling

<Practical Evaluation: Peeling Strength>

Each medical adhesive dressing was cut into a test piece having a width of 19 mm and a length of 72 mm. The cut test piece was wound around the second joint of the second finger of a hand of a volunteer so as to overlap (wrapping). After adhesion for about 24 hours, the state of the substrate or dressing was observed when the adhesive dressing was peeled off.

○: The dressing can be peeled off cleanly.

Δ: The dressing does not break during peeling, but the substrate stretches too much.

×: The substrate breaks during peeling.

<Curl>

In conducting the above practical evaluation, it was examined if the adhesive dressing curls when the release paper was peeled from each medical adhesive dressing.

○: No curl is observed, and adhesion work is easy.

Δ: Slight curl is observed, but adhesion work is not hindered.

×: One or more rounds of curl are observed, and it is extremely difficult to adhere.

<MFR, Torsional Rigidity, Pull Strength>

Measured according to JIS K-6730.

<Weight Average Molecular Weight and Molecular Weight Distribution>

Measured using 150C, a product of WATERS CO., by a high temperature gas phase chromatography (GPC) method. Measurement conditions were that three GMHHR(S) were used as a column, a column temperature was 140° C., 200 $\mu$l of o-dichlorobenzene was poured as a solvent, and measurement was made at a flow rate of 1 ml/minutes.

TABLE 1

|  | Example | | | | Comparative Example | | |
| --- | --- | --- | --- | --- | --- | --- | --- |
|  | 1 | 2 | 3 | 4 | 1 | 2 | 3 |
| Vinyl acetate Content (wt %) | 20 | 20 | 25 | 25 | 20 | — | — |
| MRF (g/10 minutes) | 1.3 | 1.3 | 2.4 | 2.4 | 1.5 | — | — |
| Mw (×10$^4$) | 8.5 | 8.5 | 6.2 | 6.2 | 9.4 | — | — |
| Mw/Mn | 3.4 | 3.4 | 2.5 | 2.5 | 4.4 | — | — |
| Substrate Thickness ($\mu$m) | 120 | 80 | 120 | 80 | 80 | 80 | 80 |

TABLE 2

|  | Example | | | | Comparative Example | | |
|---|---|---|---|---|---|---|---|
|  | 1 | 2 | 3 | 4 | 1 | 2 | 3 |
| 50% Modulus (kgf/19 mm) | 1.03 | 0.76 | 0.81 | 0.56 | 0.54 | 1.20 | 0.88 |
| Torsional Rigidity (kg/cm$^2$) | 130 | 130 | 90 | 90 | 150 | — | 128 |
| Tensile Strength (kg/19 mm) | 3.95 | 2.53 | 4.18 | 2.72 | 1.08 | 3.20 | 2.32 |
| Pull Strength (kgf/cm$^2$) | 250 | 250 | 300 | 300 | 180 | — | 235 |
| Stress Relaxation Property | 92.1 | 84.5 | 89.8 | 83.6 | 86.1 | 58.0 | 77.0 |
| Temperature-sensitivity 0° C. | ○△ | ○ | △ | ○ | ○ | X △ | ○ |
| Temperature-sensitivity 23° C. | ○ | ◎ | ○ | ◎ | ◎ | ○△ | ◎ |
| Practical Evaluation | ○ | ○ | ○ | ○ | X | ○ | △ |
| Curl | ○ | ○ | ○ | ○ | ○ | ○ | X |

INDUSTRIAL APPLICABILITY

The substrate for an adhesive dressing, medical adhesive dressing and adhesive tape, e.g., first-aid adhesive tape of the present invention comprise the ethylene/vinyl acetate copolymer having specified physical values as mentioned above, and therefore have practically satisfactory flexibility and mechanical strength, by which uncomfortable feeling during use is minimized. In particular, curl does not occur when a release paper laminated on the pressure-sensitive adhesive layer surface is peeled and removed, and thus an operating property is also excellent.

What is claimed is:

1. A substrate for an adhesive dressing, characterized by comprising an ethylene/vinyl acetate copolymer having a weight average molecular weight (Mw) of $1\times10^4$ to $1\times10^5$, a molecular weight distribution (Mw/Mn) of 4.0 or less, a melt flow rate (MFR) of 3.0 g/10 minutes or less, and a vinyl acetate content of 15 to 28% by weight.

2. The substrate for an adhesive dressing as claimed in claim 1, wherein the substrate has a thickness of 15 to 150 μm.

3. The substrate for an adhesive dressing as claimed in claim 1, wherein the substrate has a 50% modulus of 0.4 to 1.5 kgf/19 mm width and a tensile strength of 1.3 kg/19 mm width or more.

4. The substrate for an adhesive dressing as claimed in claim 1, wherein the substrate is obtained by molding into a sheet form by a calendering method.

5. The substrate for an adhesive dressing as claimed in claim 2, wherein the substrate is obtained by molding into a sheet form by a calendering method.

6. The substrate for an adhesive dressing as claimed in claim 3, wherein the substrate is obtained by molding into a sheet form by a calendering method.

7. A medical adhesive dressing comprising the substrate for an adhesive dressing as claimed in claim 1 and a pressure-sensitive adhesive layer formed on one side of said substrate.

8. An adhesive tape comprising the medical adhesive dressing as claimed in claim 1 and a pad for protecting a wounded portion, said pad being arranged on a part of a surface of the pressure-sensitive adhesive layer of said medical adhesive dressing.

9. The substrate for an adhesive dressing as claimed in claim 1, wherein the ethylene/vinyl acetate copolymer has a vinyl acetate content of 20 to 28% by weight.

10. The substrate for an adhesive dressing as claimed in claim 1, wherein the ethylene/vinyl acetate copolymer has a vinyl acetate content of 20 to 25% by weight.

11. The substrate for an adhesive dressing as claimed in claim 1, wherein the substrate consists essentially of an ethylene/vinyl acetate copolymer having a weight average molecular weight (Mw) of $1\times10^4$ to $1\times10^5$, a molecular weight distribution (Mw/Mn) of 4.0 or less, a melt flow rate (MFR) of 3.0 g/10 minutes or less, and a vinyl acetate content of 15 to 28% by weight.

* * * * *